(12) United States Patent
Austin

(10) Patent No.: US 8,784,835 B2
(45) Date of Patent: Jul. 22, 2014

(54) METHOD FOR PRODUCING MUSCIMOL AND/OR REDUCING IBOTENIC ACID FROM AMANITA TISSUE

(71) Applicant: Trent Austin, Batesville, IN (US)

(72) Inventor: Trent Austin, Batesville, IN (US)

( * ) Notice: Subject to any disclaimer, the term of this patent is extended or adjusted under 35 U.S.C. 154(b) by 0 days.

(21) Appl. No.: 13/933,861

(22) Filed: Jul. 2, 2013

(65) Prior Publication Data

US 2014/0004084 A1    Jan. 2, 2014

Related U.S. Application Data

(60) Provisional application No. 61/666,984, filed on Jul. 2, 2012.

(51) Int. Cl.
*A61K 36/06* (2006.01)
*C12N 1/14* (2006.01)

(52) U.S. Cl.
USPC .............. 424/195.15; 435/254.1; 548/243

(58) Field of Classification Search
USPC .............. 424/195.15; 435/254.1; 548/243
See application file for complete search history.

(56) References Cited

U.S. PATENT DOCUMENTS

| 4,301,287 A * | 11/1981 | Krogsgaard-Larsen | 546/19 |
| 5,189,064 A * | 2/1993 | Blum et al. | 514/561 |
| 6,077,839 A * | 6/2000 | WoldeMussie et al. | 514/220 |

* cited by examiner

*Primary Examiner* — Rosanne Kosson
(74) *Attorney, Agent, or Firm* — Maginot, Moore & Beck, LLP

(57) ABSTRACT

A method for producing muscimol and or/reducing ibotenic acid from *Amanita* tissue, and or producing a nutritional supplement therefrom.

12 Claims, 1 Drawing Sheet

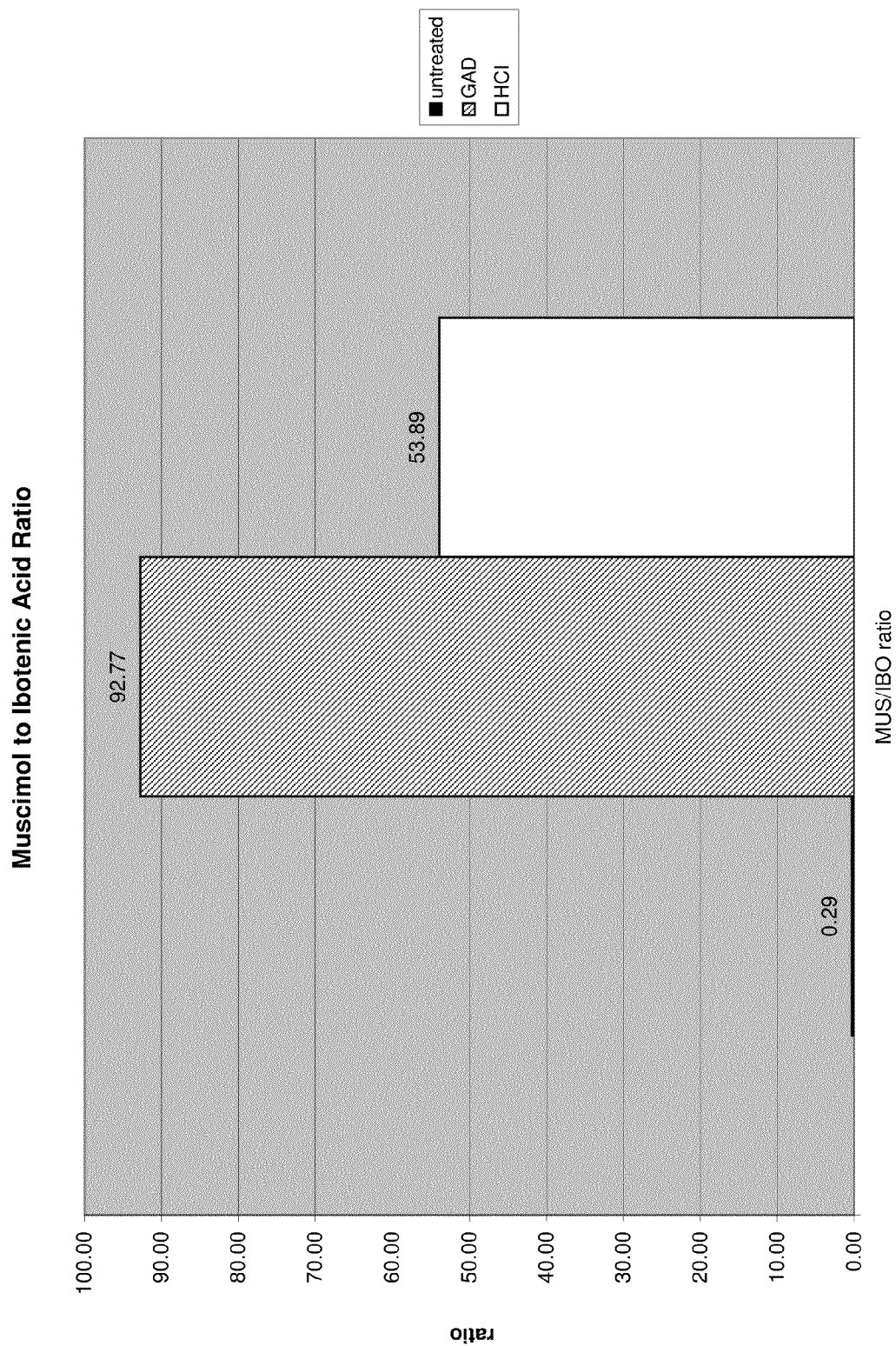

METHOD FOR PRODUCING MUSCIMOL AND/OR REDUCING IBOTENIC ACID FROM AMANITA TISSUE

The present application discloses a method for producing muscimol and or/reducing ibotenic acid from *Amanita* tissue, and or producing a nutritional supplement therefrom.

BACKGROUND

*Amanita muscaria*, and closely related fungi (i.e., *Amanita pantherina, Amanita muscaria* variant *formosa*, and others within the *Amanita* genus) contain substances that are GABA analogues and antioxidants. For example, according to at least one study, *Amanita* species were found to have "the highest antioxidant activities" among mushroom species tested.[1] However, when fresh tissue is ingested, even small amounts can cause symptoms of gastrointestinal distress (nausea, vomiting, diarrhea), headaches, profuse sweating, hypersalivation, periods of agitation and confusion, followed by coma-like sleep. These negative reactions are generally ascribed to the presence of ibotenic acid within fresh tissue, an excitatory neurotoxin. Although ibotenic acid is a neurotoxin with severe adverse effects at high concentrations, its decarboxylated variant, muscimol, is an analogue of gamma-aminobutyric acid (GABA). GABA and GABA analogues have many health benefits, including anti-aging properties, supporting the production of growth hormone, diuresis, neuroprotection, anti-hypertensive properties, and the promotion of healing.[5,6,7]

Fresh *A. muscaria* typically contains 258 to 471 ppm of ibotenic acid within the entirety of the fungi. Nearly all the ibotenic acid concentrated in the caps, and very little muscimol present.[2] Typically, the ibotenic acid to muscimol ratio of fungal cap tissue would be 9:1 or greater in fresh samples.[2] While drying of the fungal tissue has been reported to convert a portion of the ibotenic acid to muscimol, such conversion is incomplete and highly variable according to sample variation and conditions. Indeed, a relatively low conversion rate of only 30% is typical by merely drying fungal tissue, leaving an unacceptably high concentration of ibotenic acid, typically 180 to 1800 ppm.[3,4] A common ibotenic acid to muscimol ratio would be 3:2 in dried specimens[4], such that the neurotoxin amounts far exceed the GABA analogue. Furthermore, ingesting the dried tissue, which contains the relatively indigestible mushroom cell wall component chitin, would result in adverse physiological effects.

Therefore, a method to reduce the ibotenic acid in *Amanita* tissues, while maximizing water-soluble nutrients, including maximization of the GABA analogue muscimol, from a natural product, would be highly desirable.

SUMMARY

According to certain embodiments, a method for producing a dietary supplement or beverage from *Amanita* tissue comprises providing tissue from an *Amanita* fungi comprising ibotenic acid within the tissue; providing a reactant comprising glutamate decarboxylase; combining the tissue and reactant such that the ratio of muscimol to ibotenic acid increases.

According to certain embodiments, the method further comprises comminuting and drying the *Amanita* tissue prior to combining the tissue and reactant. In certain additional embodiments, the method further comprises rehydrating the tissue prior to combining the tissue and reactant. Additionally, the method may further comprise heating the tissue and reactant to a temperature of at least 175° F. In certain additional embodiments, the method further comprises heating the tissue and reactant to a temperature of at least 175° F. for at least about one hour. According to certain embodiments, the method further includes reducing the pH of the tissue and reactant below 7.0.

BRIEF DESCRIPTION OF THE DRAWINGS

FIG. 1 displays a graphical depiction of the results of the ratio of muscimol to ibotenic acid as compared to utilizing multiple embodiments according to certain aspects of the present application.

DESCRIPTION

The present disclosure relates to methods for producing a product having increased muscimol and/or ibotenic acid *Amanita* tissues (excluding *Amanita phalloides* and *Amanita virosa*). Additionally, according to certain embodiments, the present disclosure relates to products operable to act as nutritional supplements. According to one embodiment, an ingestible product is produced by the method of providing tissue from fungi. Specifically, tissue from an *Amanita* fungi is selected, preferably from the caps thereof. Thereafter, the tissue is optionally dried, freeze-dried, or otherwise dehydrated to approximately 0.3% to 5% water by weight. A distilled water extraction of the fresh or dried tissue is produced and filtered to produce a filtrate. After filtration, the filtrate is exposed to a pH above 8.0 or below 6.0, and is heated and/or refluxed for at least approximately one hour, and preferably approximately two hours, at a temperature of approximately 175° F.-200° F. Optionally, the filtrate is heated and/or refluxed at approximately 195° F.

In an alternative embodiment, the filtrate is exposed to purified glutamate decarboxylase, or a substance containing glutamate decarboxylase, and heated for 1 to 48 hours at a temperature of 90 degrees to 155 degrees F., at a pH of 3 to 6, with addition of pyridoxal 5 phosphate ("P-5-P") as a cofactor, with or without the addition of calcium chloride, magnesium sulfate, or other ions.

In yet another alternative embodiment, the filtrate is combined with one or more *Lactobacillus* bacteria such as *L plantarum, L. paracasei, L. lactis, L. brevei, L. delbrueckii*, or any other fermenting bacteria containing glutamate decarboxylase, or a substance containing glutamate decarboxylase, such as rice bran. Thereafter, according to certain embodiments, the filtrate is optionally fermented with the bacteria. According to certain embodiments, the fermented product is filtered and clarified with or without pasteurization. According to at least one embodiment, the fermented product is filtered and clarified through cotton or other filtration material, and/or filtered through an activated carbon filter.

According to certain embodiments, the filtrate is combined with one or more *Lactobacillus* bacteria such as *L plantarum, L. paracasei, L. lactis, L. brevei, L. delbrueckii*, or any other bacteria known to contain glutamate decarboxylase ("GAD"). Thereafter, the filtrate and approximately 150,000 colony forming units (CFU's) of the bacteria per ounce of filtrate are optionally adjusted to a pH of 3.8-5.5 and incubated at a temperature of approximately 98°-155° F.

According to certain embodiments, approximately 0.4 g of $CaCO_3$ or $CaCl_2$ per 64 ounces of filtrate is added, along with a prescribed amount of P-5-P as a cofactor (typically 10 mg), and approximately 4.5 teaspoons of table sugar. Initial pH of the combination of the filtrate and bacteria is approximately 6, and typically drops rapidly within 12 to 24 hours of fermentation to just under a pH of 4. After approximately 3 days of fermentation, the product is filtered, refrigerated, and clarified. The fermented, filtered product is thereafter available for use.

Bioassays of the resultant product show acceptable taste, mouthfeel, and appearance, and may be mixed with fruit juice. The resultant product did not display the undesirable effects noted in fresh *A. muscaria* tissue.

EXAMPLE 1

According to one exemplary embodiment, *Amanita* tissue was manually cleaned to remove debris, and was thereafter shade-dried in a dehydrator for approximately 36 hours at 155 degrees F. Thereafter, the dried tissue was inspected after drying to verify it is dry to approximately 0.3% to 5% water by weight. The dried tissue was then ground to a fine powder using a bun grinder. A quantity of 300 grams or more was ground per batch, and placed in a single container capable of forming a hermetic seal.

Thereafter, the dried powder was stirred for 2 minutes, then shaken in the sealed container for approximately 2 minutes to ensure homogeneity of the sample and account for differences in sample tissues. Next, 60 grams of powder were combined with 60 ounces of cold, distilled water, in a container capable of forming a hermetic seal. The combined powder in aqueous solution was then placed in a refrigerator at approximately 42 degrees F. for about 5 days, with intermittent agitation to enhance the mixture of the contents. After 5 days, the contents were filtered by pouring through a cotton sieve sized sufficiently to remove all solids contained in the mixture. The solids were then discarded, and the filtrate was combined with additional distilled water sufficient to create a total of 60 ounces, as needed.

Next, approximately 10,000,000 CFU of *Lactobacillus plantarum* (showing glutamate decarboxylase), 0.4 gram of powdered calcium carbonate, 10 mg of pyridoxal-5-phosphate, and 4.5 teaspoons of table sugar were added to the 60 ounces of aqueous filtrate. This liquid was placed in a container capable of forming a hermetic seal, stirred, secured, and the contents agitated until thoroughly mixed. The initial pH of the combined solution was approximately 6.0. Thereafter, the combined filtrate was frozen until thoroughly solid. The frozen specimen was placed in an incubator at 103° degrees F. for 3 days. An additional 10,000,000 CFU of *Lactobacillus plantarum* was added at 12 hours into fermentation. After 18 hours of fermentation, the pH dropped to approximately 3.8-4.0, and remained stable for the duration of fermentation.

The fermentation process resulted in a change from a sweet flavor to a sour flavor of the liquid. The resulting product was once again is filtered through a cotton sieve, then finally filtered through a paper filter. Further clarification with diomataceous earth was utilized with the addition of one tablespoon of diomataceous earth to the liquid, allowing it to sit refrigerated for one week, then refiltering through cotton, then a paper filter.

EXAMPLE 2

Samples of *Amanita muscaria* var. *formosa* were dried in a dehydrator for 2 days at 125 degrees Fahrenheit. The caps were selected, ground to a powder, and mixed. 240 grams of powder was effused in 60 ounces of distilled water at 45 degrees Fahrenheit for 24 hours, then filtered to remove the solid particles. Thereafter, a portion of the filtrate was diluted by adding 0.75 cc distilled water per cc of filtrate, and set aside and frozen for later analysis. This portion was retained as an untreated, or control sample, referred in the accompanying table displayed in FIG. 1 as "untreated" sample.

Additionally, a second sample, "HCl" as shown in FIG. 1, Reagent grade HCl was diluted with distilled water at a ratio of 7:1 water to HCl, and then added to a portion of the untreated, undiluted filtrate, in sufficient quantity to lower pH to 2.6. The sample was then maintained at 195 degrees to 212 degrees for 3 hours. The results of the ratio of muscimol to ibotenic acid for the HCl are shown in FIG. 1, which resulted in a ratio of 53.89 muscimol to ibotenic acid, as compared to the control sample of 0.29 muscimol to ibotenic acid.

EXAMPLE 3

Additionally, a third sample, "GAD" as shown in FIG. 1, to a portion of undiluted filtrate added 14 mg of purified glutamate decarboxylase was added to 2 ml of filtrate. 0.3 mg of pyridoxal phosphate (P-5-P) was added, and the sample was maintained at 37 degrees Celsius for 2 hours. Then the sample was held at 37 degrees Celsius for another 2 hours then refrigerated. The resultant product resulted in a ratio of muscimol to ibotenic acid is displayed as "GAD" as shown in FIG. 1, which resulted in a ratio of 92.77 muscimol to ibotenic acid, as compared to the control sample of 0.29 muscimol to ibotenic acid.

The examples above were analyzed utilizing high performance liquid chromatography ("HPLC"), following derivatization using dansylation reaction.[4] As can be seen from FIG. 1, the samples treated with GAD demonstrated excellent conversion of ibotenic acid to muscimol, with an almost 80-fold decrease in ibotenic acid, and over 300-fold increase in the muscimol to ibotenic acid ratio, versus the untreated specimen. According to certain embodiments, the reaction of muscimol tissue with GAD results in at least a 200-fold increase in muscimol to ibotenic acid ratio; at least 250-fold increase in muscimol to ibotenic acid ratio. According to certain additional embodiments, the ratio of muscimol tissue with GAD results in a ratio of muscimol to ibotenic acid of at least 90 to 1.

It will be appreciated that the resulting converted product can be filtered utilizing activated carbon filters to remove nonpolar impurities, thereby improving purity and palatability of the resulting product.

Although the invention has been described in detail with reference to preferred embodiments, variations and modifications exist within the scope and spirit of the invention.

1. Reis, Filipa S., et. al, 2011. Toward the antioxidant and chemical characterization of mycorrhizal mushrooms from northeast Portugal. Journal of Food Science Volume 76, No. 6, 824-30.
2. Tsunoda, Koujun, et. al, 1993. Simultaneous analysis of ibotenic acid and muscimol in toxic mushroom, *Amanita muscaria*, and analytical survey on edible mushrooms. Journal Food Hygienic Soc. Japan Vol 34, No. 1. 12-17.
3. Tsujikawa, Kenji, et. al, 2006. Analysis of hallucinogenic constituents in *Amanita* mushrooms circulated in Japan. Forensic Science International Vol 164, 172-178.
4. Tsujikawa, Kenji, et. al, 2007. Determination of muscimol and ibotenic acid in *Amanita* mushrooms by high-performance liquid chromatography and liquid chromatography-tandem mass spectrometry. Journal of Chromatography B 852, 430-435.
5. Cho, Yu Ran, et. al, 2007. Production of gamma-aminobutyric acid (GABA) by *Lactobacillus buch-* neri isolated from *Kimchi* and its neuroprotective effect on neuronal cells. J. Microbiol. Biotechnol. 17(1), 104-109.
6. Di Cagno, Raffaella, et. al, 2009. Synthesis of gamma-aminobutyric acid (GABA) by *Lactobacillus plantarum* DSM 19463: functional grape must beverage and dermatological applications. Applied Micorbiol. Biotechnol.
7. Levanthal, Audie, et. al, 2005. GABA and its agonists improved visual cortical function in senescent monkeys. Science, 300, 812-15.

What is claimed is:

1. A method for producing a liquid dietary supplement from *Amanita* tissue, the method comprising:
   a. providing tissue comprising an *Amanita fungus* comprising ibotenic acid within the tissue;
   b. providing a reactant comprising an enzymatically effective amount of glutamate decarboxylase;
   c. combining the tissue and reactant such that the ratio of muscimol to ibotenic acid increases; and
   d. adding the reaction product of step (c) to a beverage to make the liquid dietary supplement.

2. The method of claim 1, further comprising comminuting and drying the *Amanita* tissue prior to combining the tissue and reactant.

3. The method of claim 2, wherein the method further comprises rehydrating the tissue prior to combining the tissue and reactant.

4. The method of claim 3, further comprising heating the tissue and reactant to a temperature of at least 175° F.

5. The method of claim 4, further comprising heating the tissue and reactant to a temperature of at least 175° F. for at least about one hour.

6. The method of claim 4, wherein the tissue and reactant are reacted at a pH below 7.0.

7. The method of claim 6, further comprising filtering the resultant product.

8. The method of claim 7, wherein the filtering occurs through activated carbon.

9. The method of claim 4, wherein the resultant product has a ratio of muscimol to ibotenic acid that is at least 300 times greater than this ratio in the tissue of claim 1, step (a).

10. The method of claim 4, wherein the resultant product has a muscimol to ibotenic acid ratio of at least 75 to 1.

11. The method of claim 1, wherein the tissue comprises *Amanita muscaria*.

12. A method for producing a liquid dietary supplement from *Amanita* tissue, the method comprising:
   a. providing tissue comprising an *Amanita fungus* comprising ibotenic acid within the tissue;
   b. comminuting and drying the tissue;
   c. reconstituting the tissue of step (b);
   d. subjecting the reconstituted tissue of step (c) to a pH below 4.5;
   e. subjecting the reconstituted tissue of step (d) to heat above 175° F.; and
   f. adding the reconstituted tissue of step (e) to a beverage to make the liquid dietary supplement.

* * * * *